US006943754B2

(12) United States Patent
Aughey et al.

(10) Patent No.: US 6,943,754 B2
(45) Date of Patent: Sep. 13, 2005

(54) GAZE TRACKING SYSTEM, EYE-TRACKING ASSEMBLY AND AN ASSOCIATED METHOD OF CALIBRATION

(75) Inventors: John H. Aughey, St. Louis, MO (US); Michael V. Rohr, Fenton, MO (US); Steven D. Swaine, St. Charles, MO (US); Carl J. Vorst, St. Ann, MO (US)

(73) Assignee: The Boeing Company, Chicago, IL (US)

( * ) Notice: Subject to any disclaimer, the term of this patent is extended or adjusted under 35 U.S.C. 154(b) by 89 days.

(21) Appl. No.: 10/259,103

(22) Filed: Sep. 27, 2002

(65) Prior Publication Data

US 2004/0061831 A1 Apr. 1, 2004

(51) Int. Cl.$^7$ .............................. G09G 5/00; G09B 9/02; G09B 9/08; A61B 3/14
(52) U.S. Cl. .................... 345/8; 345/7; 345/9; 348/115; 348/117; 348/121; 434/44; 382/103; 351/205
(58) Field of Search ................................. 351/200, 205, 351/206, 209, 210, 221; 353/28, 30, 39, 46, 121, 122; 345/700, 7, 8, 9; 600/558; 382/103; 348/115, 116, 121, 135; 434/44

(56) References Cited

U.S. PATENT DOCUMENTS

| | | | |
|---|---|---|---|
| 4,034,401 A | | 7/1977 | Mann |
| 4,634,384 A | * | 1/1987 | Neves et al. .................... 434/44 |
| 4,852,988 A | * | 8/1989 | Velez et al. .................. 351/210 |
| 4,902,116 A | | 2/1990 | Ellis |
| 4,993,788 A | | 2/1991 | Steward |
| 5,331,149 A | | 7/1994 | Spitzer et al. |
| 5,487,665 A | | 1/1996 | Lechner et al. |
| 5,583,335 A | | 12/1996 | Spitzer et al. |
| 5,585,813 A | | 12/1996 | Howard |
| 5,746,599 A | | 5/1998 | Lechner |
| 5,822,127 A | | 10/1998 | Chen et al. |
| 6,120,461 A | * | 9/2000 | Smyth .......................... 600/558 |
| 6,140,980 A | * | 10/2000 | Spitzer et al. .................. 345/8 |
| 6,359,601 B1 | * | 3/2002 | Maguire, Jr. .................... 345/7 |
| 6,448,944 B2 | * | 9/2002 | Ronzani et al. ................. 345/8 |
| 6,456,438 B1 | * | 9/2002 | Lee et al. .................... 359/630 |
| 6,574,352 B1 | * | 6/2003 | Skolmoski .................. 382/103 |
| 2002/0105482 A1 | | 8/2002 | Lemelson et al. |
| 2002/0130875 A1 | * | 9/2002 | Blackham et al. .......... 345/545 |

FOREIGN PATENT DOCUMENTS

GB      2 259213 A      3/1993

OTHER PUBLICATIONS

M. Yamada, T. Fukuda, M. Hirota; *Development of an eye–movement analyzer possessing functions for wireless transmission and autocalibration*; Jul. 1990; pp. 317–324; vol. 28, No. 4; Medical and Biological Engineering & Computing; Peter Peregrinus Ltd., Stevenage, GB; XP000136092; ISSN: 0140–0118.

Laurence R. Young, David Sheena; *Methods & Designs—Survey of eye movement recording methods*; 1975; pp. 397–429; vol. 7, No. 5, Behavior Research Methods and Instrumentation, Austin Texas; XP000770072.

Qiang Ji, Zhiwei Zhu; *Eye and Gaze Tracking for Interactive Graphic Display*; Int. Symp. on Smart Graphics; Jun. 2002; 7 pages; ACM 1–58113–216–Jun. 7, 2002; Hawthorne, New York.

* cited by examiner

Primary Examiner—Brian L. Casler
Assistant Examiner—John R. Sanders
(74) Attorney, Agent, or Firm—Alston & Bird LLP (57) ABSTRACT

A system for tracking a gaze of an operator includes a head-mounted eye tracking assembly, a head-mounted head tracking assembly and a processing element. The head-mounted eye tracking assembly comprises a visor having an arcuate shape including a concave surface and an opposed convex surface. The visor is capable of being disposed such that at least a portion of the visor is located outside a field of view of the operator. The head-mounted head tracking sensor is capable of repeatedly determining a position of the head to thereby track movement of the head. In this regard, each position of the head is associated with a position of the at least one eye. Thus, the processing element can repeatedly determine the gaze of the operator, based upon each position of the head and the associated position of the eyes, thereby tracking the gaze of the operator.

19 Claims, 6 Drawing Sheets

GAZE TRACKING SYSTEM, EYE-TRACKING ASSEMBLY AND AN ASSOCIATED METHOD OF CALIBRATION

FIELD OF THE INVENTION

The present invention relates generally to head/eye tracking systems for visual display systems and, more particularly, to head/eye tracking systems including an eye tracking device having a curved visor.

BACKGROUND OF THE INVENTION

Visual display systems, such as flight simulation systems, are commonly employed to train military and commercial pilots. Conventional visual display systems include one or more screens onto which a video image is projected by one or more projectors containing image sources, such as cathode ray tubes (CRTs). The operator of the visual display system is also generally provided with a control panel and, in some instances, a joystick for providing input to the visual display system in response to the displayed video image. In this regard, the control panel and joystick are often designed to duplicate the controls and displays found in an aircraft. Thus, the operator can simulate the flight of an aircraft, for example, and can respond to the environment as depicted by the visual display.

In order to provide a relatively large display for the operator, the video image produced by the projector of a conventional flight simulation system is generally expanded and displayed upon a screen having a much larger surface area than the surface of the image source. For example, each optical line pair of a conventional projector generally defines a projection angle of 7 to 12 arcminutes. Thus, while a relatively large image is displayed for the operator, the resolution of the image is somewhat diminished by the expansion of the video image.

To improve the effective resolution of the projected video image, systems and methods have been developed to inset a high resolution video image into the displayed video image or background image. The high resolution inset image is generally relatively small and is, for example, positioned at an area of interest, such as the portion of the screen that the operator is currently viewing. The high resolution inset image generally has a small relative size, taking advantage of the human visual system's limited ability to see clear images outside a small area surrounding the line of sight. The small region surrounding the line of sight corresponds to the foveal region of the human eye and, therefore, the corresponding ability to see high detail in the region surrounding the line of sight is typically referred to as foveal vision. This high resolution inset image, which is positioned to generally follow the operator's line of sight, is typically referred to as the Area of Interest (AOI) display. The line of sight including the foveal vision of the operator is generally defined by (1) the direction the operator's head faces, and (2) the direction the operator's eyes face relative to the position of the operator's head.

Figure 1:
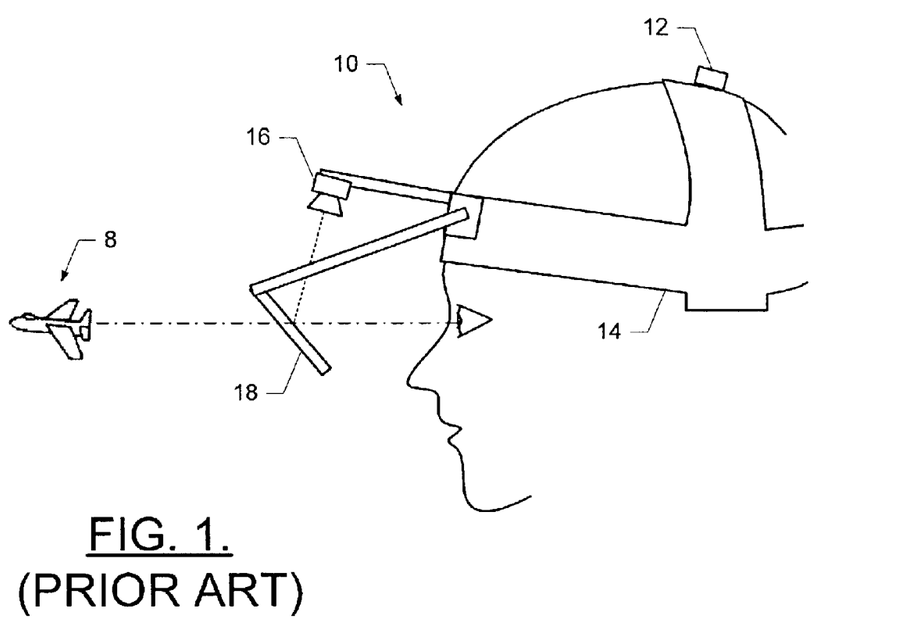
FIG. 1 is a schematic illustration of portions of a conventional gaze tracking system.

An area of interest 8 is typically determined by a head/eye tracking device, as shown in FIG. 1. As shown, to track the operator's head position, the head/eye tracking device 10 includes a head tracker sensor 12 mounted above the operator's head by means of a headband 14, helmet, or other securing device worn on the operator's head so that the position of the head/eye tracking device is held fixed in position and orientation relative to the operator's head. To track the position of the operator's eyes, the head/eye tracking device includes a video camera 16 mounted above and forward of the operator's head by means of the headband or other head-mounted securing device. The image capture device tracks the position of the operator's eyes by imaging the pupils of the operator's eyes through a partially reflective/partially transmissive flat mirror 18, which is mounted in front of the operator's eyes. By imaging the operator's pupils through the mirror, the image capture device can be mounted in a position out of the operator's visual field of view. In operation, before the head/eye tracking device 10 can track position of the operator's head and eyes, the head/eye tracking device must be calibrated with the screen upon which the video image produced by the projector is displayed. According to one conventional method of calibrating the head/eye tracking device, a plurality of calibration points are displayed upon the screen, such as nine calibration points displayed in a 3×3 matrix. Then, to calibrate the head tracker sensor 12 of the head/eye tracking device, the operator moves his head and, thus, the head tracker sensor such that one of the calibration points is in line with a fixed reference point attached to the head/eye tracker. A data point is then recorded based upon the position of the head tracker sensor. The operator then repeats the process for each of the calibration points displayed upon the screen, with a data point recorded at each calibration point. Once a data point has been recorded for all calibration points, a head tracking calibration function is calculated based upon the recorded data points.

Either before or after calibrating the head tracker sensor, the image capture device of the head/eye tracker must be calibrated with the screen so that the head/eye tracking device can accurately track the position of the operator's eyes relative to the head tracker sensor. To calibrate the image capture device, the calibration points are again displayed upon the screen. The operator then orients his head and, thus the head tracker sensor, in a fixed position, preferably such that the operator's line of sight intersects a center point of the screen. Holding his head in the fixed position, the operator moves his eyes such that the operator's line of sight intersects one of the calibration points. A data point is then recorded for the calibration point based upon an image of the operator's pupils taken by the image capture device. In this regard, the data point can include information such as pupil position in both the X and Y directions, as well as corneal reflection in both the X and Y directions. Also as before, the operator repeats the process of moving his eyes to each calibration point and recording a data point for each calibration point, all while holding his head in the fixed position. And after the data points have been recorded for all of the calibration points, an eye tracking calibration function is calculated based upon the recorded data points, e.g., (eye pitch, eye yaw)=f(input data from tracker).

After calculating the calibration functions, the head/eye tracking device tracks the position of the operator's head based upon the position of the operator's head as determined by the head tracker sensor, and based upon the head tracking calibration function. Similarly, the head/eye tracking device tracks the position of the operator's eyes as determined by the image capture device, and based upon the eye tracking calibration function. And based upon the position of the operator's head and pupils at any given time, the area of interest is selected relative to the screen and thereafter displayed, such as in line with the operator's line of sight. The high resolution inset image can then be projected within the area of interest to thereby be within the operator's foveal vision.

Whereas conventional head/eye tracking devices are adequate in tracking the head and eye position of the operator, such conventional tracking devices have drawbacks. The partially reflective/partially transmissive flat mirror 18, which is mounted in front of the operator's eyes, is visually distracting for the operator. In this regard, the mirror is an unnatural obstruction in the operator's visual field of view, limiting the operator's feeling of visual immersion in a virtual reality application, such as that found in flight simulation systems.

In addition to the structural drawback of the partially reflective/partially transmissive flat mirror 18, the method by which conventional head/eye tracking devices are calibrated also has drawbacks. As stated before, either the operator's eyes or head must remain in a fixed position for a period of time during various stages of calibrating the head/eye tracking device. In this regard, the calibration method is prone to errors caused by inadvertent movement of either the operator's eyes or head during a time in which the eyes or head must remain in a fixed position for complete accuracy. Due to the time period the operator is required to keep either his eyes or head in the fixed position, the operator can have a tendency to fatigue, which can cause the operator's eyes or head to inadvertently move.

SUMMARY OF THE INVENTION

In light of the foregoing background, the present invention therefore provides an improved eye-tracking assembly, gaze tracking system and method of calibration. According to the present invention, the eye-tracking assembly includes a visor that, at least a portion of which, is capable of being located outside the central field of view of the operator. As such, the operator can utilize the eye-tracking assembly, as well as the gaze tracking system and method of calibration, without distractions associated with conventional eye-tracking assemblies. In this regard, the visor of the eye-tracking assembly can provide a more natural environment to an operator, such as a pilot, that would typically wear a visor that encompasses the operator's field of view.

Also, according to embodiments of the present invention, the method of calibrating a gaze tracking system includes calibrating the system based upon a relative position of both the operator's head and eyes. Also, the method of calibration includes movement of the head tracking sensor with the operator's eyes aligned in a particular direction, as opposed to fixing the head in position and aligning the operator's line of sight with several reference points. As such, the method of the present invention provides a more accurate technique for calibrating the gaze tracking system. Further, the method can utilize an artificial neural network to calibrate the system based upon input data from an eye-tracking assembly and head tracking sensor. Thus, the system can adaptively learn from previous movements, as opposed to deriving a conventional static calibration function.

According to one aspect of the present invention, a system for tracking a gaze of an operator includes a head-mounted eye tracking assembly, a head-mounted head tracking assembly and a processing element. The head-mounted eye tracking assembly comprises a visor having an arcuate shape including a concave surface and an opposed convex surface. The visor is capable of reflecting an image of at least one eye. For example, the concave surface of the visor can include a reflective coating. In this regard, the visor is capable of being disposed such that the operator's eye are located proximate the concave side such that an image of the eyes is reflected thereby. Advantageously, the visor is capable of being disposed such that at least a portion of the visor is located outside a field of view of the operator. The eye tracking assembly can further include an illuminator capable of illuminating the eyes, such as with infrared light. In operation, then, the head-mounted eye tracking assembly is capable of repeatedly determining a position of the eyes based upon the image of the eyes reflected by the visor to thereby track movement of the eyes.

More particularly, to track movement of the eyes based upon the image of the eyes reflected by the visor, the head-mounted eye tracking assembly can further comprise a camera disposed proximate the concave surface of the visor. For example, the eye tracking assembly can include a camera that is located outside the field of view of the operator. To more precisely operate the camera, the head-mounted eye tracking assembly can also include a lens disposed in an optical path of the camera. The effective focus of the camera can then be based upon the optical power of the visor and the optical power of the lens.

The head-mounted head tracking sensor is capable of repeatedly determining a position of the head to thereby track movement of the head. In this regard, each position of the head is associated with a position of the at least one eye. As such, the processing element can repeatedly determine the gaze of the operator based upon each position of the head and the associated position of the eyes. Thus, the processing element can repeatedly determine the gaze of the operator to thereby track the gaze of the operator.

According to another aspect of the present invention, a method is provided for calibrating the gaze tracking system relative to an object. The method typically begins by repeatedly moving the head and, thus, the head tracking sensor, to a plurality of different positions. Before moving the head, however, the line of sight of the eyes can be aligned with the first reference point. Similarly, a position of the head tracking sensor can be set as the second reference position. At each position, then, a position of the eyes and an angle offset from the line of sight of the eyes relative to a first reference point are both measured. Also, the position of the head tracking sensor and the angle by which the head tracking sensor is offset relative to a second reference position is measured. The gaze tracking system is then calibrated based upon the measured positions of the at least one eye, the offset angles of the at least one eye, the positions of the head tracking sensor and the offset angles of the head tracking sensor relative to the second reference position. Advantageously, the gaze tracking system can also be calibrated with an artificial neural network or according to an interpolation technique.

BRIEF DESCRIPTION OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 2:
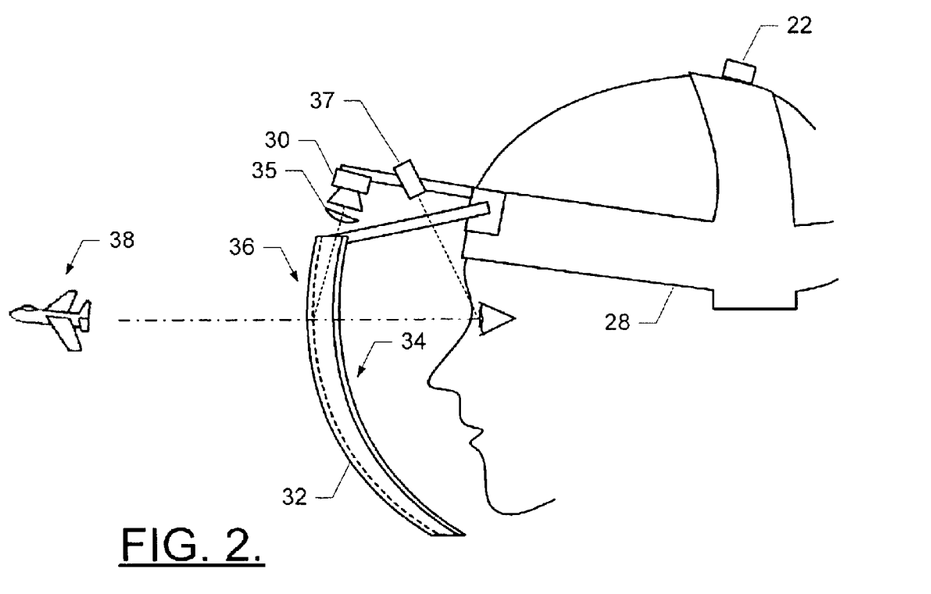
FIG. 2 is a schematic illustration of portions of a gaze tracking system according to one embodiment of the present invention.
Figure 3:
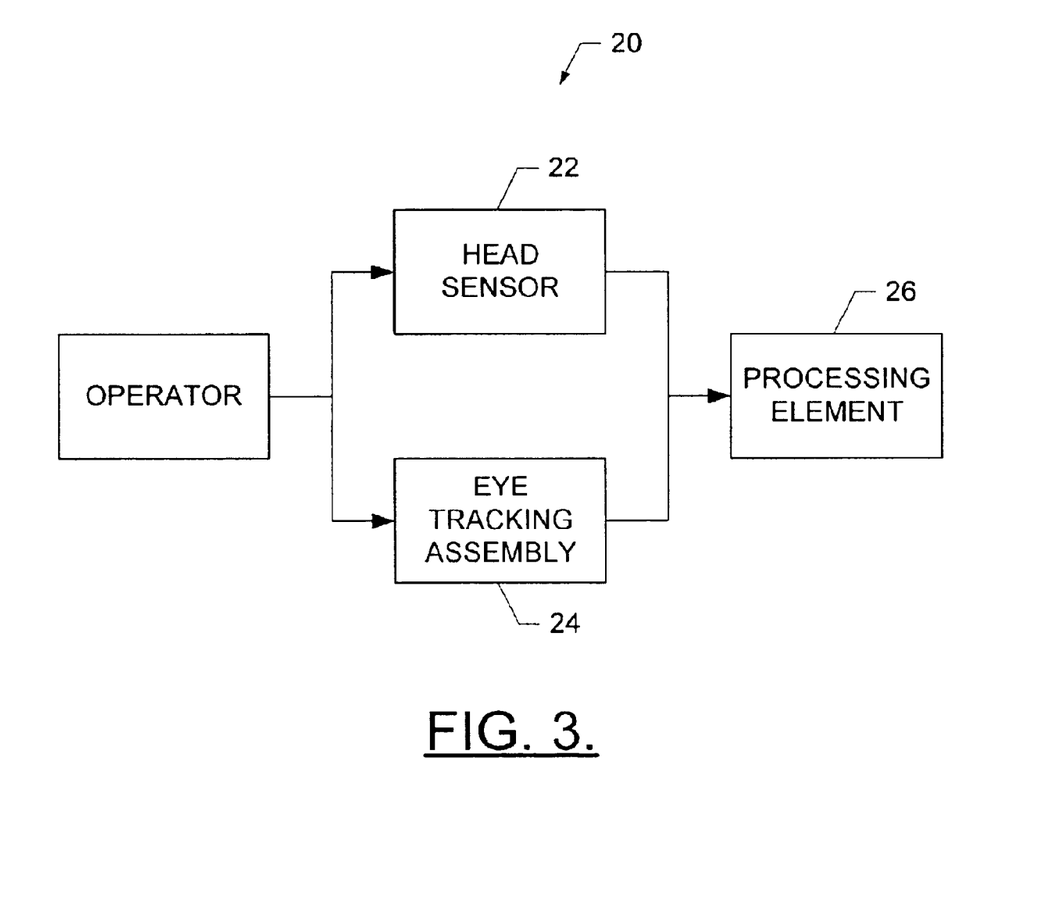
FIG. 3 is a block diagram of a gaze tracking system according to one embodiment of the present invention.

Referring to FIGS. 2 and 3, a gaze tracking system 20 according to one embodiment of the present invention is shown. The system includes a head-mounted head tracking sensor 22, a head-mounted eye tracking assembly 24, and a processing element 26. The head tracking sensor and eye tracking assembly are mounted to an operator's head by means of a headband 28, helmet or other head-mounted securing device. The head tracking sensor is mounted to the operator's head out of the field of vision of the operator so as to not impede the operator's vision. The head tracking sensor is capable of repeatedly determining a position of the operator's head to thereby track the movement of the head. In this regard, the head tracking sensor can comprise any of a number of known sensors capable of determining the position of the operator's head. For example, the head tracker sensor can comprise an InsideTrak model head tracking sensor or a FasTrak model head tracking sensor, both manufactured by Polhemus Incorporated of Colchester, Vt. Alternatively, the head tracker sensor can comprise any of a number of other head tracking sensors that operate based on magnetic, acoustic, optical or other technologies, as such are known to those skilled in the art.

The eye tracking assembly comprises an image capture device 30 and a visor 32. The visor is secured to the headband 28 such that, when the headband is mounted to the operator's head, the visor is disposed in front of the operator's head. The visor is preferably at least partially reflective for light of a predetermined wavelength or range of wavelengths. For example, the visor may be made from a partially reflective material, such as Lexan brand polycarbonate (manufactured by the General Electric Company of Pittsfield, Mass.) coated with a reflective film, so that the operator's field of view can extend through the visor while an image of the operator's eyes, or more particularly the operator's pupils, reflects off of the visor into the optical path of the image capture device. Advantageously, the visor is designed to provide an environment for the operator that is typically found in many applications employing the system, such as flight simulation applications. In this regard, the visor is designed to not present any visually obstructive edges with the operator's field of view. Thus, the visor has an arcuate or curved shape including a concave surface 34 and an opposed convex surface 36, one of which may support an at least partially reflective coating. The visor is secured to the headband such that, when the headband is mounted to the operator's head, the concave surface is disposed proximate the operator's eyes. Further, the visor is secured to the headband such that, when the headband is mounted to the operator's head, at least a portion of the visor is located outside the operator's field of view.

Like the head tracking sensor 22, the image capture device 30 is mounted outside the field of view of the operator so as to not impede the operator's vision. In this regard, the image capture device is preferably mounted on a front portion of the headband 28 such that the image capture device is located at a position peripheral to the operator's head out of the operator's field of view. The image capture device is capable of repeatedly determining a position of the operator's eyes by imaging the pupil of one or both of the operator's eyes. Because the image capture device is mounted on the headband outside the field of view of the operator, the image capture device images the operator's pupils by imaging a reflection of the pupils from the visor of the eye tracking assembly. Thus, the image capture device can comprise any of a number of devices capable of repeatedly determining the position of the operator's eyes to thereby track the movement of the operator's eyes. According to one embodiment, for example, the image capture device comprises a camera, such as is included within ETL-500 model eye tracking system manufactured by ISCAN, Inc. of Burlington, Mass.

Advantageously, the image capture device 30 can comprise a camera, such as is used in a conventional head/eye tracking device including a partially reflective/partially transmissive flat mirror 18, as shown in FIG. 1. But it will be appreciated that the visor 32 of the present invention will typically have a different optical power than the flat mirror of the conventional head/eye tracking device. In this regard, lenses have a characteristic power that is typically measured in diopters and equals the inverse of the focal length of the lens in meters, as such is known to those skilled in the art. It will also be appreciated that, in using a camera such as is used in a conventional head/eye tracking device, the effective focus of the camera will differ from the desired effective focus due to the difference in optical power between the visor and the conventional flat mirror. Thus, in embodiments where the image capture device comprises a camera such as is used in a conventional head/eye tracking device, the system preferably compensates for the change effective focus due to the difference in optical power so as to bring the effective focus to a desired value, or the value of the effective focus of the camera as used in the conventional head/eye tracking device.

The system 20 can compensate for the optical power of the visor 32 in any of a number of different manners. For example, the aperture of the camera lens can be reduced to thereby increase the depth-of-field of the camera. And by increasing the depth-of-field of the camera, the system can compensate for the change in effective focus of the camera. Additionally or alternatively, the system can include a lens 35 disposed in the optical path of the camera to compensate for the optical power of the visor. In this regard, if the aperture of the camera lens is not reduced, the lens can be selected such that the optical power of the lens plus the optical power of the visor equals the optical power of a flat mirror as would be included in a conventional head/eye tracking device including the camera.

As previously stated, the image capture device 30 images the operator's pupils by receiving light reflected off of the pupils and thereafter off of the visor 32 into the optical path of the image capture device. To facilitate tracking the eyes, the system 20 can include an illuminator 37 capable of illuminating the eyes such that more light reflects off of the eyes and, thus, the visor. However, to avoid visual distractions, the illuminator is preferably an infrared illuminator, such as an infrared light emitting diode, capable of illuminating infrared light to the eyes. The infrared light, thus, reflects off of the front and rear surfaces of the corneas and the lenses of the eyes, and thereafter reflects off of the visor into the optical path of the camera. It will be appreciated that such images are commonly referred to as Purkinje images by those skilled in the art. It will also be appreciated that as the light in this embodiment comprises infrared light, the image capture device of this embodiment is preferably infrared sensitive, such as an infrared sensitive camera. Additionally, the predetermined wavelength or range of wavelengths that the visor is capable of reflecting advantageously includes infrared light in this embodiment.

To track the gaze of the operator based upon a position of the operator's eyes and head, the system 20 also includes a processing element 26. The processing element can comprise any of a number of different devices, such as a personal computer or other high level processor. As shown in FIG. 3, and as already stated, the eye-tracking assembly is capable of determining a position of the operator's eyes. Similarly, the head tracking sensor 22 is capable of determining a position of the operator's head. The processing element 26, in turn, is capable of receiving the position of the operator's eyes from the eye-tracking assembly and the position of the operator's head from the head tracking sensor. Based upon the position of the operator's eyes and operator's head, the processing element can determine the operator's gaze. Repeatedly receiving the position of the operator's eyes and head, the processing element can therefore track the operator's gaze, as will be appreciated by those skilled in the art. And based upon the gaze of the operator the processing element can define an area of interest 38 (shown in FIG. 2) relative to an external device, such as a display.

Before the system can track the gaze of the operator, the system 20 is preferably calibrated to the external device, such as a display. As previously indicated, the difficulty in calibrating conventional eye trackers is that any head movement during calibration will cause an error in the calibration. Thus, embodiments of the present invention provide a method of calibrating a gaze tracking system, such as the gaze tracking system described above, using data from the head tracking sensor 22. By using data from the head tracking sensor, then, the calibration can compensate for any head movement, and the true gaze angle can be determined more accurately.

Advantageously, embodiments of the method of the present invention also uses movement of the head tracking sensor during calibration to collect eye data. In this regard, conventional eye tracker calibration methods commonly calibrate the eye tracker based upon a set of calibration points that typically numbers less than ten. Conventional calibration methods, then, are typically limited to a small number of data points (i.e., input parameters) by which to approximate a calibration function for the eye tracker. As such, the more data points that are recorded, and the more distributed the data points, the better the final calibration of the eye tracker. Whereas any of a number of different techniques can be employed to collect data points, embodiments of the present invention provide are capable of collecting a large number of data points during calibration, as described below.

Figure 4A:
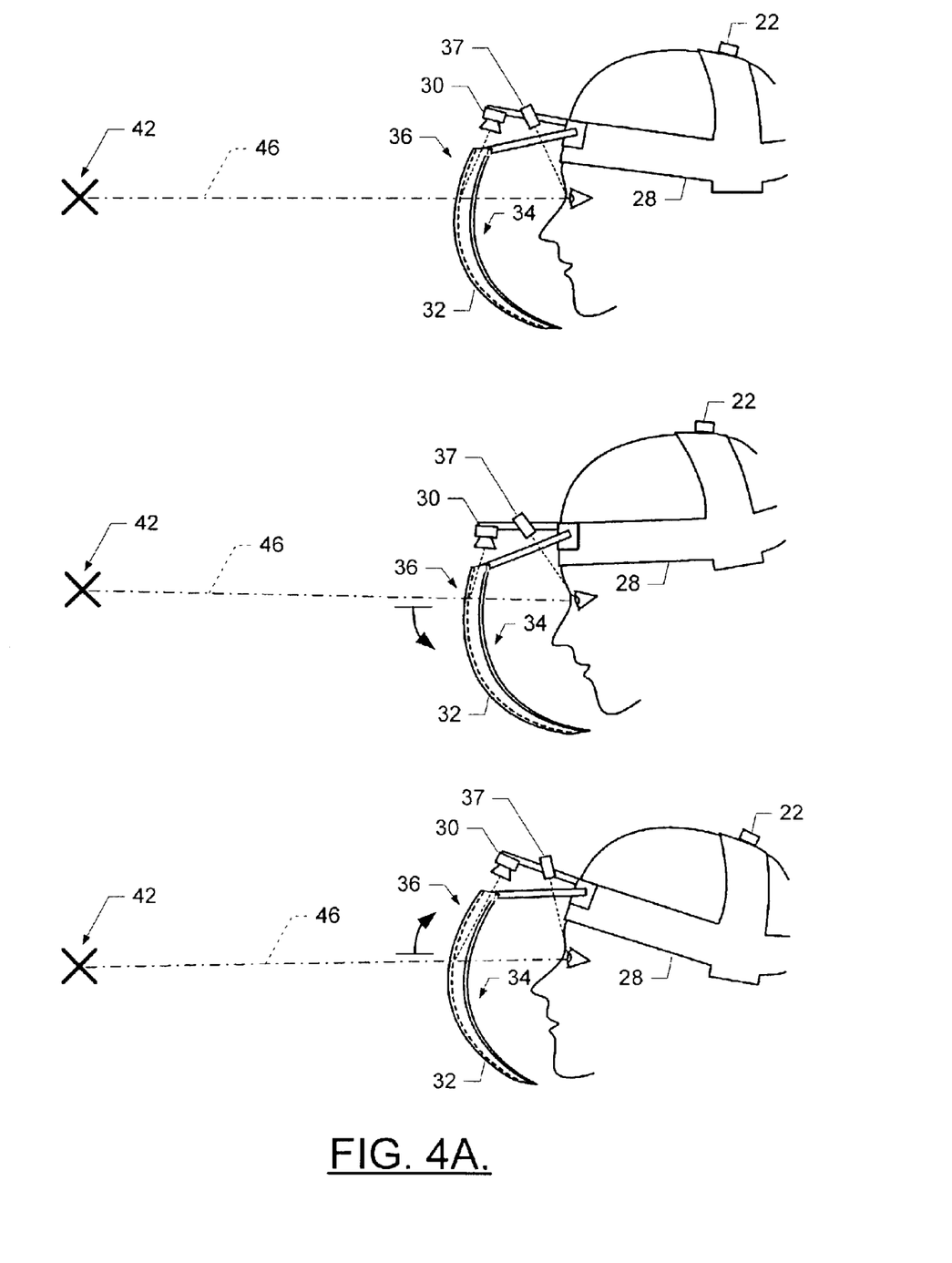
FIGS. 4A and 4B are schematic illustrations illustrating various movements in a method for calibrating the gaze tracking system according to one embodiment of the present invention.
Figure 4B:
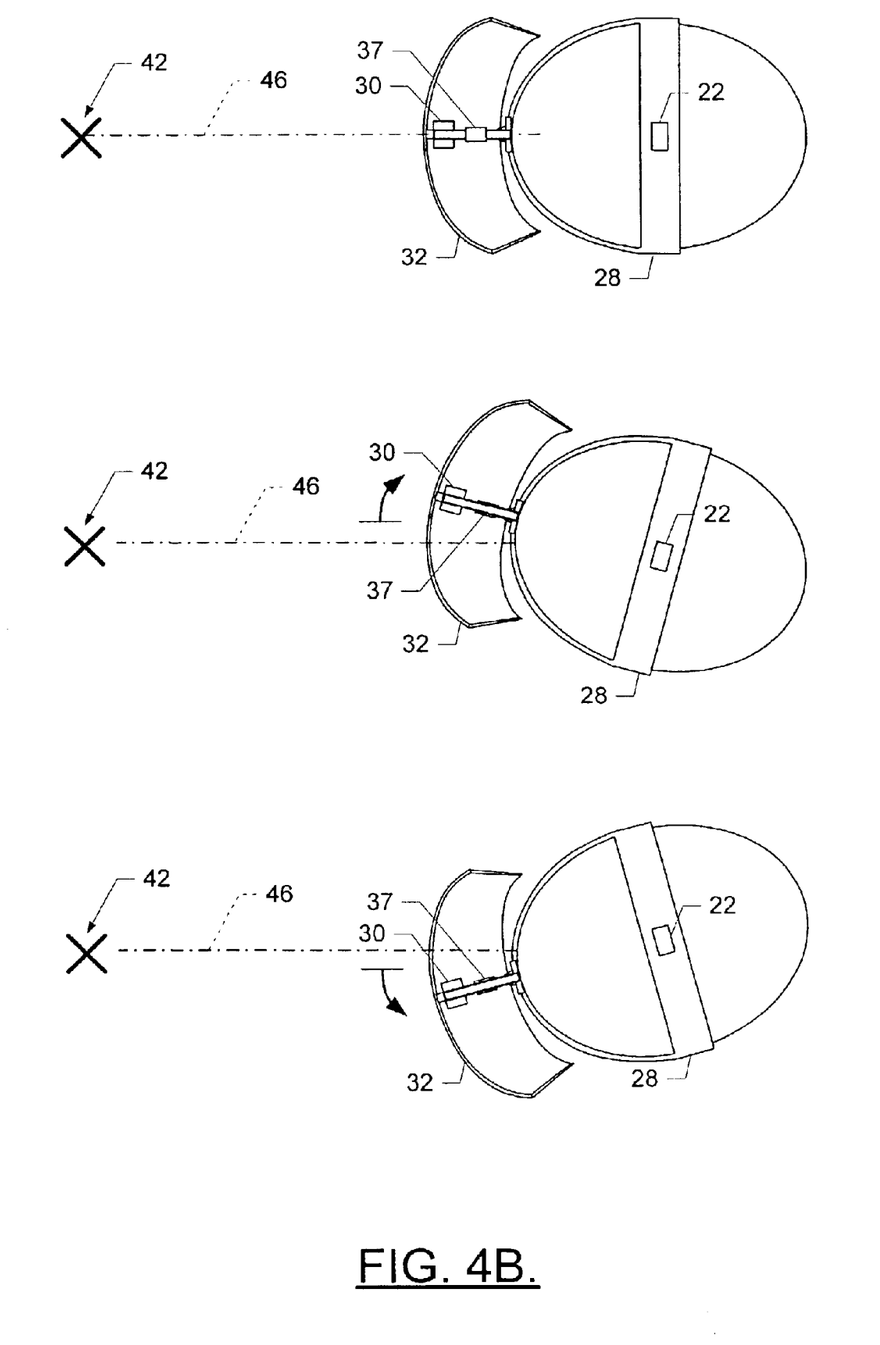
Figure 5:
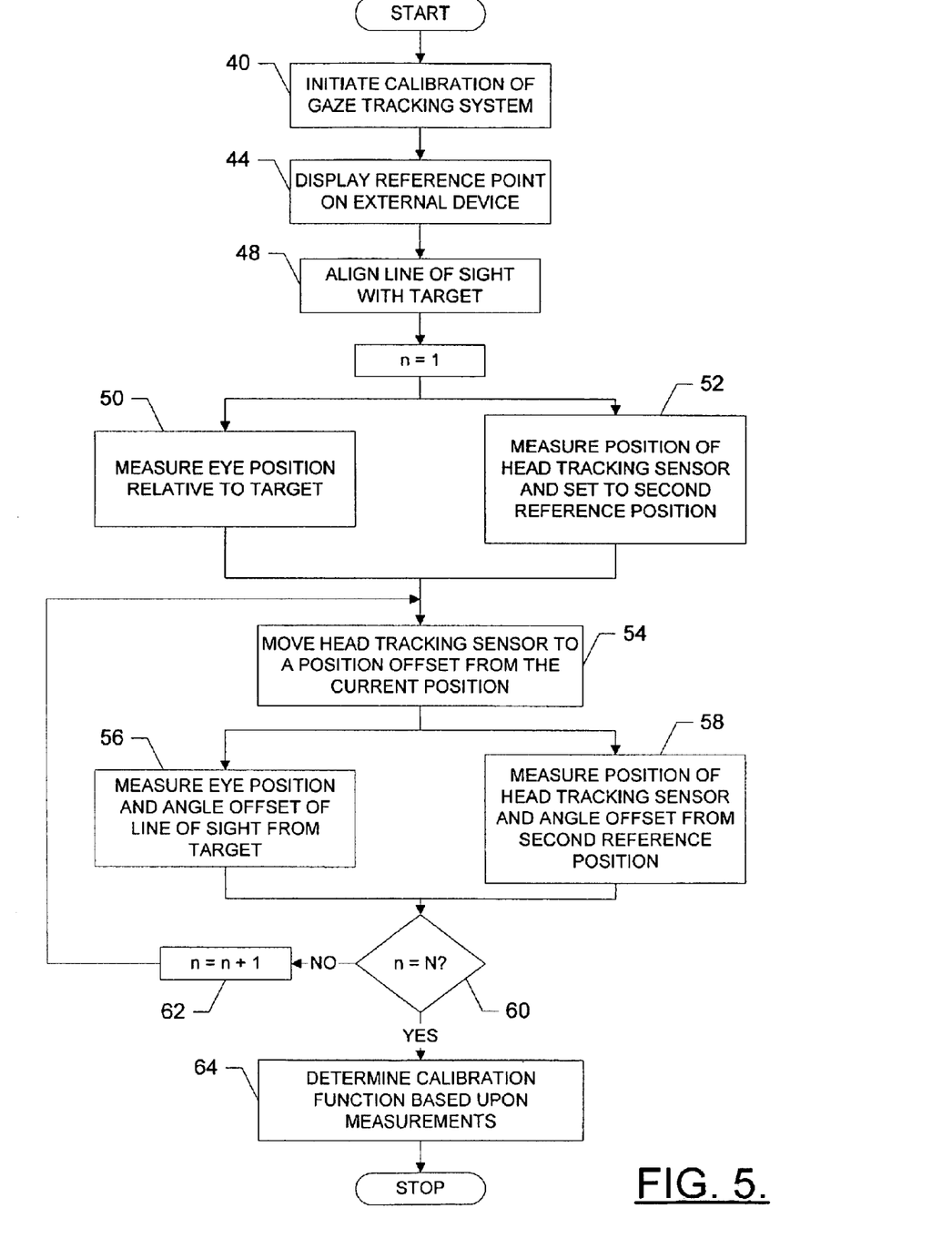
FIG. 5 is a flow chart illustrating various steps in a method of calibrating a gaze tracking system according to one embodiment of the present invention.

Referring now to FIGS. 4A, 4B and 5, the method of calibrating the gaze tracking system begins with initializing calibration of the gaze tracking system, as shown in block 40 of FIG. 5. Initialization can be accomplished according to any of a number of different manners but, according to one embodiment, calibration of the system is initialized by initiating a calibration routine within the processing element 26. Once calibration of the system has been initialized, the processing element can drive a display to present a first reference point 42, or target, within the operator's field of view, as shown in FIGS. 4A, 4B and block 44 of FIG. 5.

Once the target 42 has been presented to the operator, the operator aligns the operator's line of sight 46 with the displayed target, as shown in block 48 of FIG. 5. The operator then begins the calibration process, such as by actuating the processing element 26 to begin calibration of the system. In this regard, when the operator actuates the processing element, the processing element drives the eye tracking assembly to measure the position of the operator's eyes, which measurement the processing element will then associate with the target, as shown in block 50. At the same time, the processing element drives the head tracking sensor 22 to measure the angle of the operator's head as well as translations of the position of the operator's head, as shown in block 52. The measured angle and translations are then set by the processing element to be a second reference position.

After the position of the operator's eyes and head have been measured by the gaze tracking system 20, while keeping the operator's line of sight 46 aligned with the target 42, the operator moves the operator's head and, thus, the head tracking sensor 22, to a position offset from the second reference position, as shown in FIGS. 4A and 4B, and block 54 of FIG. 5. In keeping the operator's line of sight aligned with the target while the operator moves the operator's head, the operator's eyes generally move opposite of the head to maintain alignment of the line of sight with the target. Once at the offset position, then, the gaze tracking system measures the position of the eyes and an angle offset of the line of sight of the eyes relative to the first reference point, as shown in block 56. Similarly, the gaze tracking system measures the position of the head tracking sensor or, more particularly, the angle of the operator's head and translations of the position of the operator's head relative to the second reference position, as shown in block 58. Next, the processing element 26 records the positions, such as in a memory location. Also, the processing element can determine the direction of the operator's eyes relative to the operator's head from the measurements, and record the direction along with the measurements.

After the processing element 26 has recorded the measurements and the direction of the operator's eyes, the operator then moves the operator's head to another offset position, again keeping the line of sight 46 aligned with the target 42. The gaze tracking system again measures the position of the eyes and head tracking sensor 22, and records the measurements along with the direction of the operator's eyes. The process continues for N (e.g., 300) movements of the operator's head such that the processing records N data points consisting of the recorded measurements and directions of the operator's eyes relative to the operator's head, as shown in blocks 60 and 62 of FIG. 5. Advantageously, the operator can move the operator's head to different offset positions, and the processing element can correspondingly record measurements, at a high rate, such as 60 times a second. As such, large amounts of data can be collected in a short amount of time. For example, recording measurements at a rate of 60 times a second, the processing element can record 300 measurements in five seconds. In comparison, it would require roughly ten second to collect data from a nine point grid of calibration points using conventional methods.

Allowing the operator to move the operator's head freely while aligning the line of sight 46 with the target 42 allows a large amount of data to be collected in a short amount of time. But such a method typically gives very little control over what data is collected. For example, since the operator can move his head in any way the operator chooses, the recorded data can become concentrated in a small area, such as around the target. For most calibration functions, the more distributed the data, the better the resulting calibration. Thus, to allow for more control over the data that is collected, the processing element 26 can be capable of moving the target to one or more different positions. And after moving the target to each position, the operator again aligns the line of sight and moves the head tracking sensor 22 to different offset positions, with the processing element collecting data at each position. Whereas the processing element can move the target to any one of a number of different points, the processing element preferably moves the target to areas on a reference plane (e.g., display screen) for which the processing element has fewer recorded measurements.

With the data points, then, the processing element 26 determines a calibration function to thereby calibrate the gaze tracking system 20. the processing element can determine the calibration function according to any one of a number of different methods. For example, the processing element can determine the calibration function according to an interpolation method using an interpolation function, such as akima interpolation, b-spline interpolation, bi-cubic interpolation, linear interpolation quadratic interpolation, or the like. In such functions, the set of data points are used as reference points and intermediate points, between the data points, are determined, or interpolated, based on the surrounding data points.

According to one advantageous embodiment, the processing element determines the calibration function utilizing an artificial neural network, as illustrated in block 64 of FIG. 5. As is known to those skilled in the art, artificial neural networks are modeled upon the human brain's interconnected system of neurons. Based upon this premise, the artificial neural network allows the processing element to imitate the brain's ability to sort out patterns and learn from trial and error, discerning and extracting the relationships that underlie the input data. The network learns when the input data (with known results) is presented to processing element. Factors associated with the known results are then adjusted to bring the calibration output closer to the known result (e.g., position relative to the target).

In addition to the above identified methods of determining the calibration function, the processing element can use known physical properties of the optics of the eye tracking assembly 24 of the gaze tracking system 20, and/or the physical properties of the operator's eyes (e.g., curvature of the eyes), to determine the calibration function. In this regard, the above methods of determining the calibration function allow for any unknown distortion to be present in the input data. For example, due to the curvature of the visor 32, the image capture device 30 may receive and/or record an image of the pupils of the operator's eyes that has some degree of radial distortion. Embodiments of the calibration method of the present invention can at least partially compensate for the distortion by estimating the calibration function for the data. However, using the known physical properties of the optics, the processing element can further compensate for any optical distortion. For example, the processing element can further compensate for optical distortion by computing the light path through the system and mapping out any irregularities according to any of a number of known techniques.

Figure 6:
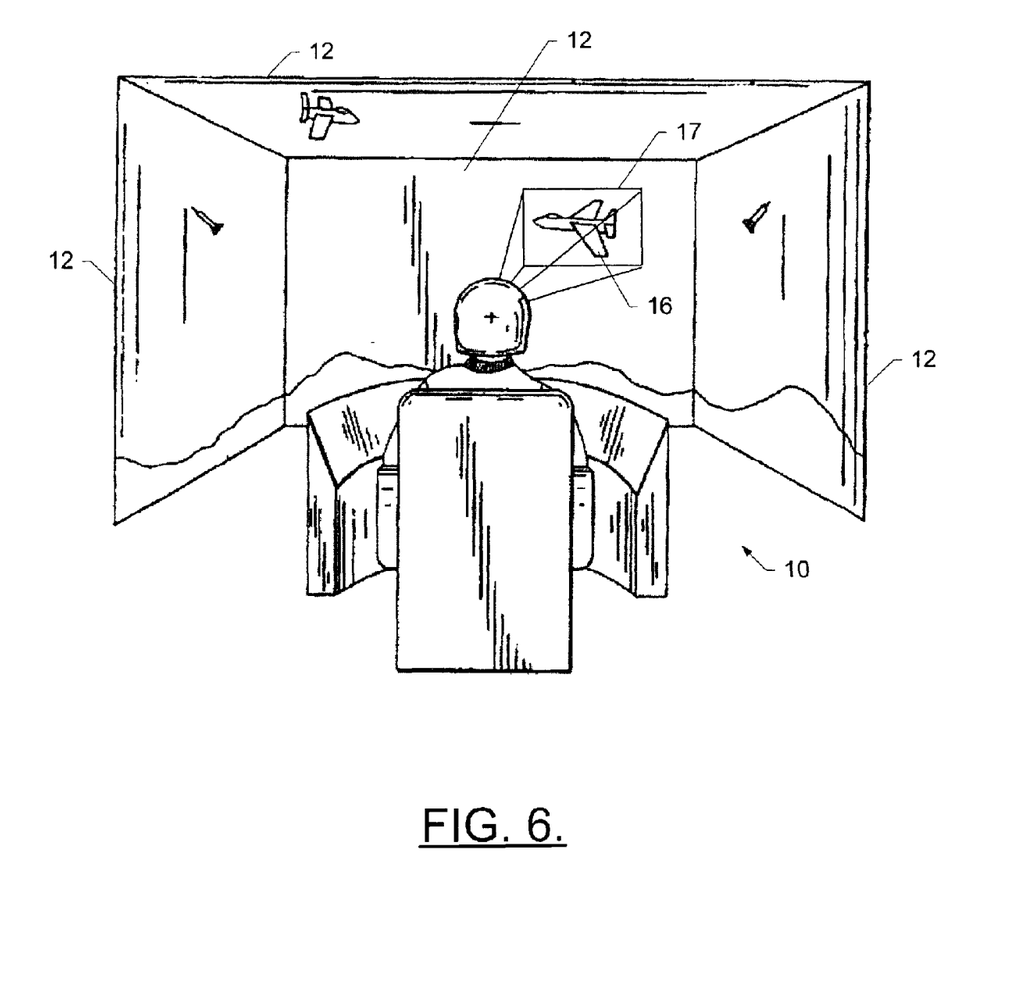
FIG. 6 is a perspective view illustrating a visual display system incorporating the gaze tracking system of one embodiment of the present invention.

Referring now to FIG. 6, a visual display system 10, such as a flight simulation system, that would benefit from the gaze tracking system of the present invention is illustrated. The visual display system generally includes a plurality of display screens 12. For example, the visual display system can include an out-the-window flight simulation system such as the Visual Integrated Display System manufactured by The Boeing Company, the assignee of the present application. As also illustrated in FIG. 6, the image displayed on the display screens 12 includes a background image having a predetermined size and resolution. The background image is generally generated by a background image projector. The background image projector can, and preferably does, include a plurality of background image projectors, at least one of which is associated with each display screen. For full color background images, the background image projectors are generally RGB projector.

In order to display a relatively large background image for the operator, the individual pixels are projected, and thereby expanded, for display on the associated display screen 12. For example, each pair of video lines typically defines a projection angle of 7 to 12 arcminutes. Therefore, the resulting background image displayed on the display screens has a relatively low resolution. As illustrated in FIG. 6, an inset image 16 can also be displayed on the display screen and is generally generated by an inset image projector. As shown, the inset image can include other aircraft in an area of interest (AOI) 17 of the operator. Each inset image (i.e., AOI image) preferably has a smaller size and a higher resolution than the background image in order to provide the operator with additional detail in this particular AOI. The AOI is defined by the gaze of the operator and, as such, the visual display system includes a gaze tracking system, such as a gaze tracking system 20 in accordance with the present invention (shown in FIGS. 2–4), to track the gaze of the operator. For more information on such a display system, see U.S. Pat. No. 5,487,665 or U.S. Pat. No. 5,746,599, the contents of both of which are hereby incorporated by reference in their entirety.

Therefore, the present invention provides an improved eye-tracking assembly, gaze tracking system and method of calibration. In this regard, by including a visor, at least a portion of which is capable of being located outside the field of view of the operator, the operator can utilize the eye-tracking assembly without distractions associated with conventional eye-tracking assemblies. As such, the visor of the eye-tracking assembly can provide a more native environment to an operator, particularly in instances in which the operator would typically wear a visor that encompasses the operator's field of view. Also, the present invention provides an improved method of calibrating a gaze tracking system. The method of calibration includes movement of the head tracking sensor with the operator's eyes aligned in a particular direction, as opposed to fixing the head in position and aligning the operator's line of sight with several reference points. As such, the method provides a more accurate technique for calibrating the gaze tracking system. Further, the method can utilize an artificial neural network to calibrate the system based upon input data from an eye-tracking assembly and head tracking sensor, which allows the neural network to adaptively learn from previous movements.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A head-mounted eye tracking assembly for tracking movement of at least one eye of an operator, said eye tracking assembly comprising:
 a visor having an arcuate shape including a concave surface and an opposed convex surface, wherein said visor is capable of being disposed such that the at least one eye is located proximate the concave surface, wherein said visor is at least partially reflective such that said visor is capable of reflecting an image of the at least one eye, and wherein said visor is capable of being disposed such that at least a portion of said visor is located outside a field of view of the operator;
 an image capture device disposed proximate the concave surface of said visor, wherein said image capture device is capable of tracking movement of the at least one eye based upon the image of the at least one eye reflected by said visor; and
 a lens disposed in an optical path of said image capture device wherein an effective focus of said image capture device is based upon an optical power of said visor and an optical power of said lens.

2. A head-mounted eye tracking assembly according to claim 1, wherein the concave surface of said visor includes a reflective coating.

3. A head-mounted eye tracking assembly according to claim 1, further comprising an illuminator capable of illuminating the at least one eye.

4. A head-mounted eye tracking assembly according to claim 3, wherein said illuminator is capable of illuminating the at least one eye with infrared light.

5. A head-mounted eye tracking assembly according to claim 1, wherein said image capture device is located outside the field of view of the operator.

6. A head-mounted eye tracking assembly according to claim 1, wherein said visor is capable of reflecting an image of a pupil of at least one eye, and wherein said image capture device is capable of tracking movement of the at least one eye based upon the image of the pupil of the at least one eye.

7. A system for tracking a gaze of an operator, said gaze tracking system comprising:
 a head-mounted eye tracking assembly comprising:
  a visor having an arcuate shape including a concave surface and opposed an convex surface, wherein said visor is capable of being disposed such that the at least one eye is located proximate the concave side, wherein said visor is at least partially reflective such that said visor is capable of reflecting an image of the at least one eye, wherein said visor is capable of being disposed such that at least a portion of said visor is located outside a field of view of the operator, and wherein the head-mounted eye tracking assembly is capable of repeatedly determining a position of the at least one eye based upon the image of the at least one eye reflected by said visor to thereby track movement of the at least one eye;
  an image capture device disposed proximate the concave surface of said visor, wherein the image capture device is capable of tracking movement of the at least one eye based upon the image of the at least one eye reflected by said visor; and
  a lens disposed in an optical path of the image capture device, wherein an effective focus of the image capture device is based upon an optical power of the visor and an optical power of the lens;
 a head-mounted head tracking sensor capable of repeatedly determining a position of the head to thereby track movement of the head, wherein each position of the head associated with a position of the at least one eye; and
 a processing element capable of repeatedly determining the gaze of the operator to thereby track the gaze of the operator, wherein said processing element repeatedly determines the gaze of the operator based upon each position of the head and the associated position of the at least one eye.

8. A system according to claim 7, wherein the concave surface of the visor of said head-mounted eye tracking assembly includes a reflective coating.

9. A system according to claim 7, wherein said head-mounted eye tracking assembly further comprises an illuminator capable of illuminating the at least one eye.

10. A system according to claim 9, wherein the illuminator is capable of illuminating the at least one eye with infrared light.

11. A system according to claim 7, wherein the image capture device located outside the field of view of the operator.

12. A system according to claim 7, wherein said visor is capable of reflecting an image of a pupil of at least one eye, and wherein the head-mounted eye tracking assembly is capable of repeatedly determining a position of the at least one eye based upon the image of the pupil of the at least one eye.

13. A visual display system comprising:
 a background image projector having a predetermined field of view, said background image projector generating a background image having a predetermined size an resolution that at least partially fills the field of view;
 at least one inset image projector for generating an area of interest (AOI) image having a smaller size and a higher resolution than the background image, said inset image projector having a predetermined field of view that is capable of being movably disposed at least partially within the field of view of said background image projector; and
 a gaze tracking system capable of directing the movement of the field of view of said inset image projector based upon the direction in which an operator is looking, said gaze tracking system comprising a head-mounted eye tracking assembly comprising:
  a visor having an arcuate shape including a concave surface and an opposed convex surface, wherein said visor is capable of being disposed such that the at least one eye is located proximate the concave surface, wherein said visor is at least partially reflective such that said visor is capable of reflecting an image of the at east one eye, and wherein said visor is capable of being disposed such that at least a portion of said visor is located outside a field of view of the operator;
  an image capture device disposed proximate the concave surface of said visor, wherein said image capture device is capable of tracking movement of the at least one eye based upon the image of the at least one eye reflected by said visor;
  a lens disposed in an optical path of said image capture device, wherein an effective focus of said image capture device is based upon an optical power of said visor and an optical power of said lens.

14. A visual display system according to claim 13, wherein said gaze tracking system further comprises:
 a head-mounted head tracking sensor capable of repeatedly determining a position of the head to thereby track movement of the head, wherein each position of the head is associated with a position of the at least one eye; and a processing element capable of repeatedly determining the gaze of the operator to thereby track the gaze of the operator, wherein said processing element repeatedly determines the gaze of the operator based upon each position of the head and the associated position of the at least one eye.

15. A visual display system according to claim 13, where the concave surface of the visor of said head-mounted eye tracking assembly includes a reflective coating.

16. A visual display system according to claim 13, wherein said head-mounted eye tracking assembly further comprises an illuminator capable of illuminating the at least one eye.

17. A visual display system according to claim 13, wherein said head-mounted eye tracking assembly further comprises a lens disposed in an optical path of said image capture device, wherein an effective focus of said image capture device is based upon an optical power of said visor and an optical power of said lens.

18. A visual display system according to claim 13, wherein said visor is capable of reflecting an image of a pupil of at least one eye, and wherein said image capture device is capable of tracking movement of the at least one eye based upon the image of the pupil of the at least one eye.

19. A visual display system according to claim 13, wherein said inset image projector has a predetermined field of view that is capable of being movably disposed based upon electronic raster deflection.

* * * * *